US011592444B2

(12) United States Patent
Loos

(10) Patent No.: US 11,592,444 B2
(45) **Date of Patent: *Feb. 28, 2023**

(54) DETECTION OF AUTOANTIBODIES AGAINST THE TSH RECEPTOR

(71) Applicant: Ulrich Loos, Ulm (DE)

(72) Inventor: Ulrich Loos, Ulm (DE)

( * ) Notice: Subject to any disclaimer, the term of this patent is extended or adjusted under 35 U.S.C. 154(b) by 4 days.

This patent is subject to a terminal disclaimer.

(21) Appl. No.: 15/320,437

(22) PCT Filed: Jun. 17, 2015

(86) PCT No.: PCT/EP2015/063627

§ 371 (c)(1),
(2) Date: Dec. 20, 2016

(87) PCT Pub. No.: WO2015/193387

PCT Pub. Date: Dec. 23, 2015

(65) Prior Publication Data

US 2018/0209973 A1 Jul. 26, 2018

(30) Foreign Application Priority Data

Jun. 20, 2014 (EP) .................................... 14173341
Aug. 11, 2014 (DE) ..................... 10 2014 011 653.0

(51) Int. Cl.
*G01N 33/564* (2006.01)
*C07K 14/72* (2006.01)
*G01N 33/543* (2006.01)
*G01N 33/76* (2006.01)

(52) U.S. Cl.
CPC ......... *G01N 33/564* (2013.01); *C07K 14/723* (2013.01); *G01N 33/54326* (2013.01); *G01N 33/76* (2013.01)

(58) Field of Classification Search
None
See application file for complete search history.

(56) References Cited

U.S. PATENT DOCUMENTS 8,809,003 B2 * 8/2014 Wei .................... G01N 21/6428 435/7.9
2009/0325310 A1 * 12/2009 Loos ................... C07K 14/723 436/500

FOREIGN PATENT DOCUMENTS

WO 00/00590 1/2000
WO 2007036511 A1 4/2007

OTHER PUBLICATIONS

Tahara K et al. “Epitopes for Thyroid Stimulating and Blocking Autoantibodies on The Extracellular Domain of the Human Thyrotropin Receptor,” Thyroid. vol. 7, No. 6, 1997.

* cited by examiner

*Primary Examiner* — G. R. Ewoldt
(74) *Attorney, Agent, or Firm* — Honigman LLP; Fernando Alberdi; Jonathan P. O’Brien

(57) ABSTRACT

The invention relates to a bridge assay that can be used on an automatic diagnostic apparatus in order to detect anti-thyrotropin receptor autoantibodies, wherein the chimeric TSH receptor used comprises the extracellular portion of the chimeric TSH receptor and is N-terminally fused to a protein causing secretion of the chimeric TSH receptor from culture cells, and the anchored chimeric TSH receptor is immobilized on paramagnetic particles.

6 Claims, 5 Drawing Sheets

Specification includes a Sequence Listing.

3.1

3.2

Standard curve in the comparative example

SEQUENCE LISTING

```
<160> NUMBER OF SEQ ID NOS: 6

<210> SEQ ID NO 1
<211> LENGTH: 1728
<212> TYPE: DNA
<213> ORGANISM: Artificial Sequence
<220> FEATURE:
<223> OTHER INFORMATION: Synthetically Generated Sequence

<400> SEQUENCE: 1

gatatcctag cttttctctt ctgtcaaccc cacacgcctt tggcacagat atcacaatga     60
agtgggtaac ctttatttcc cttctttttc tctttagctc ggcttattcc aggggtgtgt    120
ttcgtcgaga tgcacacaag agtgaggttg ctcatcggtt taaagatttg ggagaagaaa    180
atttcaaagc cttggtgttg attgcctttg ctcagtatct tcagcagtgt ccatttgaag    240
atcatgtaaa attagtgaat gaagtaactg aatttgcaaa aacatgtgtt gctgatgagt    300
cagctgaaaa ttgtgacaaa tcacttcata cccttttttgg agacaaatta tgcacagttg    360
caactcttcg tgaaacctat ggtgaaatgg ctgactgctg tgcaaaacaa gaacctgaga    420
gaaatgaatg cttcttgcaa cacaaagatg acaacccaaa cctcccccga ttggtgagac    480
cagaggttga tgtgatgtgc actgcttttc atgacaatga agagacattt ttgaaaaaat    540
acttatatga aattgccaga agacatcctt acttttatgc cccggaactc cttttctttg    600
ctaaaaggta taaagctgct tttacagaat gttgccaagc tgctgataaa gctgcctgcc    660
tgttgccaaa gctcactagt ggaatggggt gttcgtctcc accctgcgag tgccatcagg    720
aggaggactt cagagtcacc tgcaaggata ttcaacgcat ccccagctta ccgcccagta    780
cgcagactct gaagcttatt gagactcacc tgagaactat tccaagtcat gcattttcta    840
atctgcccaa tatttccaga atctacgtat ctatagatgt gactctgcag cagctggaat    900
```

```
cacactcctt ctacaatttg agtaaagtga ctcacataga aattcggaat accaggaact    960

taacttacat agaccctgat gccctcaaag agctccccct cctaaagttc cttggcattt   1020

tcaacactgg acttaaaatg ttccctgacc tgaccaaagt ttattccact gatatattct   1080

ttatacttga aattacagac aaccccttaca tgacgtcaat ccctgtgaat gcttttcagg   1140

gactatgcaa tgaaaccttg acactgaagc tgtacaacaa tggctttact tcagtccaag   1200

gatatgcttt caatgggaca aagctggatg ctgtttacct aaacaagaat aaatacctga   1260

cagttattga caaagatgca tttggaggag tatacagtgg accaagcttg ctggacgtgt   1320

ctcaaaccag tgtcactgcc cttccatcca aaggcctgga gcacctgaag gaactgatag   1380

caagaaacac ctggactctt aagaaaaacac tgccctccaa agaaaaattc acgagcctcc   1440

tggtcgccac gctgacctac cccagccact gctgcgcctt caggaatttg ccgaagaaag   1500

aacagaattt ttcattttcc atttttgaaa acttctccaa acaatgcgaa agcacagtta   1560

gaaaagcaga taacgagacg ctttattccg ccatctttga ggagaatgaa gctagcatct   1620

gtaaacgcca ggctcaggca taccgggggc agagggttcc tccaaagaac agcactgata   1680

ttcaggttca aaaggttacc taaggatcca ctagtcagtg tgctggaa                1728
```

<210> SEQ ID NO 2
<211> LENGTH: 548
<212> TYPE: PRT
<213> ORGANISM: Artificial Sequence
<220> FEATURE:
<223> OTHER INFORMATION: Synthetically Generated Sequence

<400> SEQUENCE: 2

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Thr Ser
        195                 200                 205

Gly Met Gly Cys Ser Ser Pro Pro Cys Glu Cys His Gln Glu Glu Asp
    210                 215                 220
```

```
Phe Arg Val Thr Cys Lys Asp Ile Gln Arg Ile Pro Ser Leu Pro Pro
225                 230                 235                 240

Ser Thr Gln Thr Leu Lys Leu Ile Glu Thr His Leu Arg Thr Ile Pro
                245                 250                 255

Ser His Ala Phe Ser Asn Leu Pro Asn Ile Ser Arg Ile Tyr Val Ser
            260                 265                 270

Ile Asp Val Thr Leu Gln Gln Leu Glu Ser His Ser Phe Tyr Asn Leu
        275                 280                 285

Ser Lys Val Thr His Ile Glu Ile Arg Asn Thr Arg Asn Leu Thr Tyr
    290                 295                 300

Ile Asp Pro Asp Ala Leu Lys Glu Leu Pro Leu Leu Lys Phe Leu Gly
305                 310                 315                 320

Ile Phe Asn Thr Gly Leu Lys Met Phe Pro Asp Leu Thr Lys Val Tyr
                325                 330                 335

Ser Thr Asp Ile Phe Phe Ile Leu Glu Ile Thr Asp Asn Pro Tyr Met
            340                 345                 350

Thr Ser Ile Pro Val Asn Ala Phe Gln Gly Leu Cys Asn Glu Thr Leu
        355                 360                 365

Thr Leu Lys Leu Tyr Asn Asn Gly Phe Thr Ser Val Gln Gly Tyr Ala
    370                 375                 380

Phe Asn Gly Thr Lys Leu Asp Ala Val Tyr Leu Asn Lys Asn Lys Tyr
385                 390                 395                 400

Leu Thr Val Ile Asp Lys Asp Ala Phe Gly Gly Val Tyr Ser Gly Pro
                405                 410                 415

Ser Leu Leu Asp Val Ser Gln Thr Ser Val Thr Ala Leu Pro Ser Lys
            420                 425                 430

Gly Leu Glu His Leu Lys Glu Leu Ile Ala Arg Asn Thr Trp Thr Leu
        435                 440                 445

Lys Lys Thr Leu Pro Ser Lys Glu Lys Phe Thr Ser Leu Leu Val Ala
    450                 455                 460

Thr Leu Thr Tyr Pro Ser His Cys Cys Ala Phe Arg Asn Leu Pro Lys
465                 470                 475                 480

Lys Glu Gln Asn Phe Ser Phe Ser Ile Phe Glu Asn Phe Ser Lys Gln
                485                 490                 495

Cys Glu Ser Thr Val Arg Lys Ala Asp Asn Glu Thr Leu Tyr Ser Ala
            500                 505                 510

Ile Phe Glu Glu Asn Glu Ala Ser Ile Cys Lys Arg Gln Ala Gln Ala
        515                 520                 525

Tyr Arg Gly Gln Arg Val Pro Pro Lys Asn Ser Thr Asp Ile Gln Val
    530                 535                 540

Gln Lys Val Thr
545
```

<210> SEQ ID NO 3
<211> LENGTH: 240
<212> TYPE: PRT
<213> ORGANISM: Artificial Sequence
<220> FEATURE:
<223> OTHER INFORMATION: Synthetically Generated Sequence

<400> SEQUENCE: 3

```
Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30
```

```
Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu Glu Ile Thr Asp Asn Pro Tyr Met
    130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
        195                 200                 205

Ser Leu Leu Asp Val Ser Gln Thr Ser Val Thr Ala Leu Pro Ser Lys
    210                 215                 220

Gly Leu Glu His Leu Lys Glu Leu Ile Ala Arg Asn Thr Trp Thr Leu
225                 230                 235                 240


<210> SEQ ID NO 4
<211> LENGTH: 310
<212> TYPE: PRT
<213> ORGANISM: Artificial Sequence
<220> FEATURE:
<223> OTHER INFORMATION: Synthetically Generated Sequence

<400> SEQUENCE: 4

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu Glu Ile Thr Asp Asn Pro Tyr Met
    130                 135                 140

Thr Ser Ile Pro Val Asn Ala Phe Gln Gly Leu Cys Asn Glu Thr Leu
145                 150                 155                 160
```

```
Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
        195                 200                 205

Ser Leu Leu Asp Val Ser Gln Thr Ser Val Thr Ala Leu Pro Ser Lys
    210                 215                 220

Gly Leu Glu His Leu Lys Glu Leu Ile Ala Arg Asn Thr Trp Thr Leu
225                 230                 235                 240

Lys Lys Thr Leu Pro Ser Lys Glu Lys Phe Thr Ser Leu Leu Val Ala
                245                 250                 255

Thr Leu Thr Tyr Pro Ser His Cys Cys Ala Phe Arg Asn Leu Pro Lys
            260                 265                 270

Lys Glu Gln Asn Phe Ser Phe Ser Ile Phe Glu Asn Phe Ser Lys Gln
        275                 280                 285

Cys Glu Ser Thr Val Arg Lys Ala Asp Asn Glu Thr Leu Tyr Ser Ala
    290                 295                 300

Ile Phe Glu Glu Asn Glu
305                 310
```

<210> SEQ ID NO 5
<211> LENGTH: 2012
<212> TYPE: DNA
<213> ORGANISM: Artificial Sequence
<220> FEATURE:
<223> OTHER INFORMATION: Synthetically Generated Sequence

<400> SEQUENCE: 5

```
gatatcctag cttttctctt ctgtcaaccc cacacgcctt tggcacagat atcacaatga     60

agtgggtaac ctttatttcc cttctttttc tctttagctc ggcttattcc aggggtgtgt    120

ttcgtcgaga tgcacacaag agtgaggttg ctcatcggtt taaagatttg ggagaagaaa    180

atttcaaagc cttggtgttg attgcctttg ctcagtatct tcagcagtgt ccatttgaag    240

atcatgtaaa attagtgaat gaagtaactg aatttgcaaa aacatgtgtt gctgatgagt    300

cagctgaaaa ttgtgacaaa tcacttcata cccttttttgg agacaaatta tgcacagttg    360

caactcttcg tgaaacctat ggtgaaatgg ctgactgctg tgcaaaacaa gaacctgaga    420

gaaatgaatg cttcttgcaa cacaaagatg acaacccaaa cctcccccga ttggtgagac    480

cagaggttga tgtgatgtgc actgcttttc atgacaatga agagacattt ttgaaaaaat    540

acttatatga aattgccaga agacatcctt acttttatgc cccggaactc cttttctttg    600

ctaaaaggta taaagctgct tttacagaat gttgccaagc tgctgataaa gctgcctgcc    660

tgttgccaaa gctcatgagg ccggcggact tgctgcagct ggtgctgctg ctcgacctgc    720

ccagggacct gggcggaatg ggtgttcgt ctccaccctg cgagtgccat caggaggagg    780

acttcagagt cacctgcaag gatattcaac gcatccccag cttaccgccc agtacgcaga    840

ctctgaagct tattgagact cacctgagaa ctattccaag tcatgcattt tctaatctgc    900

ccaatatttc cagaatctac gtatctatag atgtgactct gcagcagctg gaatcacact    960

ccttctacaa tttgagtaaa gtgactcaca tagaaattcg gaataccagg aacttaactt   1020

acatagaccc tgatgccctc aaagagctcc ccctcctaaa gttccttggc attttcaaca   1080

ctggacttaa aatgttccct gacctgacca aagtttattc cactgatata ttctttatac   1140
```

```
ttgaaattac agacaaccct tacatgacgt caatccctgt gaatgctttt cagggactat   1200

gcaatgaaac cttgacactg aagctgtaca acaatggctt tacttcagtc caaggatatg   1260

ctttcaatgg gacaaagctg gatgctgttt acctaaacaa gaataaatac ctgacagtta   1320

ttgacaaaga tgcatttgga ggagtataca gtggaccaag cttgctggac gtgtctcaaa   1380

ccagtgtcac tgcccttcca tccaaaggcc tggagcacct gaaggaactg atagcaagaa   1440

acacctggac tcttaagaaa cttccacttt ccttgagttt ccttcacctc acacgggctg   1500

acctttctta cccaagccac tgctgtgctt ttaagaatca gaagaaaatc agaggaatcc   1560

ttgagtcctt gatgtgtaat gagagcagta tgcagagctt gcgccagaga aaatctgtga   1620

atgccttgaa tagcccccctc caccaggaat atgaagagaa tctgggtgac agcattgttg   1680

ggtacaagga aaagtccaag ttccaggata ctcataacaa cgctcattat tacgtcttct   1740

ttgaagaaca agaggatgag atcattggtt ttggccagga gctcaaaaac ccccaggaag   1800

agactctaca agcttttgac agccattatg actacaccat atgtggggac agtgaagaca   1860

tggtgtgtac ccccaagtcc gatgagttca acccgtgtga agacataatg ggctacaagt   1920

tcctgagaat ctgtaaacgc caggctcagg cataccgggg gcagagggtt cctccaaaga   1980

acagcactga tattcaggtt caaaaggtta cc                                 2012
```

```
<210> SEQ ID NO 6
<211> LENGTH: 652
<212> TYPE: PRT
<213> ORGANISM: Artificial Sequence
<220> FEATURE:
<223> OTHER INFORMATION: Synthetically Generated Sequence

<400> SEQUENCE: 6

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Met Arg
        195                 200                 205
```

```
Pro Ala Asp Leu Leu Gln Leu Val Leu Leu Leu Asp Leu Pro Arg Asp
    210                 215                 220

Leu Gly Gly Met Gly Cys Ser Ser Pro Pro Cys Glu Cys His Gln Glu
225                 230                 235                 240

Glu Asp Phe Arg Val Thr Cys Lys Asp Ile Gln Arg Ile Pro Ser Leu
                245                 250                 255

Pro Pro Ser Thr Gln Thr Leu Lys Leu Ile Glu Thr His Leu Arg Thr
            260                 265                 270

Ile Pro Ser His Ala Phe Ser Asn Leu Pro Asn Ile Ser Arg Ile Tyr
        275                 280                 285

Val Ser Ile Asp Val Thr Leu Gln Gln Leu Glu Ser His Ser Phe Tyr
    290                 295                 300

Asn Leu Ser Lys Val Thr His Ile Glu Ile Arg Asn Thr Arg Asn Leu
305                 310                 315                 320

Thr Tyr Ile Asp Pro Asp Ala Leu Lys Glu Leu Pro Leu Leu Lys Phe
                325                 330                 335

Leu Gly Ile Phe Asn Thr Gly Leu Lys Met Phe Pro Asp Leu Thr Lys
            340                 345                 350

Val Tyr Ser Thr Asp Ile Phe Phe Ile Leu Glu Ile Thr Asp Asn Pro
        355                 360                 365

Tyr Met Thr Ser Ile Pro Val Asn Ala Phe Gln Gly Leu Cys Asn Glu
    370                 375                 380

Thr Leu Thr Leu Lys Leu Tyr Asn Asn Gly Phe Thr Ser Val Gln Gly
385                 390                 395                 400

Tyr Ala Phe Asn Gly Thr Lys Leu Asp Ala Val Tyr Leu Asn Lys Asn
                405                 410                 415

Lys Tyr Leu Thr Val Ile Asp Lys Asp Ala Phe Gly Gly Val Tyr Ser
            420                 425                 430

Gly Pro Ser Leu Leu Asp Val Ser Gln Thr Ser Val Thr Ala Leu Pro
        435                 440                 445

Ser Lys Gly Leu Glu His Leu Lys Glu Leu Ile Ala Arg Asn Thr Trp
    450                 455                 460

Thr Leu Lys Lys Leu Pro Leu Ser Leu Ser Phe Leu His Leu Thr Arg
465                 470                 475                 480

Ala Asp Leu Ser Tyr Pro Ser His Cys Cys Ala Phe Lys Asn Gln Lys
                485                 490                 495

Lys Ile Arg Gly Ile Leu Glu Ser Leu Met Cys Asn Glu Ser Ser Met
            500                 505                 510

Gln Ser Leu Arg Gln Arg Lys Ser Val Asn Ala Leu Asn Ser Pro Leu
        515                 520                 525

His Gln Glu Tyr Glu Glu Asn Leu Gly Asp Ser Ile Val Gly Tyr Lys
    530                 535                 540

Glu Lys Ser Lys Phe Gln Asp Thr His Asn Asn Ala His Tyr Tyr Val
545                 550                 555                 560

Phe Phe Glu Glu Gln Glu Asp Glu Ile Ile Gly Phe Gly Gln Glu Leu
                565                 570                 575

Lys Asn Pro Gln Glu Glu Thr Leu Gln Ala Phe Asp Ser His Tyr Asp
            580                 585                 590

Tyr Thr Ile Cys Gly Asp Ser Glu Asp Met Val Cys Thr Pro Lys Ser
        595                 600                 605

Asp Glu Phe Asn Pro Cys Glu Asp Ile Met Gly Tyr Lys Phe Leu Arg
    610                 615                 620

Ile Cys Lys Arg Gln Ala Gln Ala Tyr Arg Gly Gln Arg Val Pro Pro
```

-continued

```
625                 630                 635                 640

Lys Asn Ser Thr Asp Ile Gln Val Gln Lys Val Thr
                645                 650
```

DETECTION OF AUTOANTIBODIES AGAINST THE TSH RECEPTOR

CROSS-REFERENCE

This application claims priority under 35 U.S.C. § 371 to Patent Cooperation Treaty application PCT/EP2015/063627, filed Jun. 17, 2015, which claims the benefit of EP patent application no. 14173341.0, filed Jun. 20, 2014, and DE patent application no. 10 2014 011 653.0, filed Aug. 11, 2014, the entire contents of which are incorporated herein by reference.

SEQUENCE LISTING

This application incorporates in its entirety the Sequence Listing entitled "406125 ST25.txt," which is 20.3 kilobytes in size and was created on Dec. 12, 2016 and filed electronically herewith.

TECHNICAL FIELD OF THE INVENTION

The invention relates to a method for detecting autoantibodies or autoimmune antibodies against the thyroid hormone receptor performable on a diagnostic analyzer and the use of a TSH receptor chimera, formed at least partly from a protein comprising the extracellular part of the TSH receptor and immobilized on paramagnetic particles in a bridge assay together with a further TSH receptor chimera in such a method and a modified TSH receptor chimera.

TECHNOLOGICAL BACKGROUND OF THE INVENTION

The TSH receptor (TSH-R) has a key role in the growth and function of thyroid cells. This receptor is a member of a subfamily of the G protein-coupled glycoprotein receptors, which also includes the receptors for luteinizing hormone/chorionic gonadotropin (LH/CGR) and follicle-stimulating hormone (FSHR). The receptors of this subfamily have a large N-terminal extracellular domain which is of essential importance for ligand binding and which has been shown to be in signal transmission. The transmission of the TSHR signal is predominantly mediated by activation of adenylate cyclase, which leads to an increase in the intracellular cAMP level.

Part of the major interest in the TSH receptor is attributable to its role as a primary autoantigen in thyroid autoimmune diseases which are accompanied by the occurrence of autoantibodies against the TSH receptor. Among such thyroid autoimmune diseases is Basedow's disease, an autoimmune disease leading to thyroid hyperfunction, which is among the commonest human autoimmune diseases overall. Basedow's disease is caused by activation of adenylate cyclase and a resulting increase in cAMP. This leads to thyroid hyperfunction, goiter formation and sometimes ocular changes. The autoantibodies against the TSH receptor can however also be of a blocking nature and thus inhibit the adenylate cyclase and the cAMP. In this case, hypofunction of the thyroid occurs. Simultaneous occurrence of stimulating and blocking autoantibodies in the patient affected is also possible, in which case the contribution of the stimulating autoantibody as a rule predominates.

For detecting such autoantibodies, there has for some time been a bioassay in which the increase in cAMP is measured. This measurement method is very time-consuming. In addition, the bioassay is not reliable, since it can yield false positive results. In the context of this description, this type of measurement method is described as a bioassay to distinguish it from the in vitro method for determining autoantibodies against the TSH receptor. In one in vitro detection method for autoantibodies available on the market, a TSH receptor extracted from porcine thyroid membrane is used [first creation of the in vitro method]. In another test for detecting autoantibodies against the TSH receptor, a human complete recombinant TSH receptor protein (wild type) is used in a competitive test.

Thyroid Vol. 7 (1997) 867-877 describes the epitopes for stimulating and blocking autoantibodies at the TSH receptor. The majority of the functional epitopes for stimulating autoantibodies are present in the region of the amino acids 8 to 168 and those for the blocking autoantibodies in the region of the amino acids 261 to 370 of the receptor protein. For activity measurements, the aforesaid bioassay is used.

Through WO 01/27634 A1, a quantitative method for detecting autoantibodies of different specificity in parallel, which is rapidly reproducible and performable with high precision, is for the first time provided. For this purpose, TSH receptor chimeras are used which differ from the wild type receptor in that individual sequences to which autoantibodies bind are replaced by corresponding sequences of another receptor from the class of the G protein-coupled receptors. The TSH receptor chimeras otherwise comprise the complete TSH receptor. However, the measurement cost is high. The separation by centrifugation renders the method too laborious for routine use. Also, the test must be performed in the ice bath or at 4° C., since the TSH receptor chimeras are not very stable. A similar technical teaching is to be found in WO 01/63296 A1, in which the use of a sandwich technique for the detection is proposed. However, it has been found that as a rule with the test materials proposed there the nonspecific binding is too high. A test for detecting autoantibodies on the basis of the knowledge in the two aforesaid patent applications is not obtainable on the market.

WO 00/00590 A1 describes a C-terminally truncated TSH receptor and in a general manner its suitability for diagnosis and therapy. WO 2007/036511 A1 describes a so-called bridge assay for detecting autoantibodies against the TSH receptor, which for the first time can be performed on an automatic device. To perform this bridge assay, two TSH receptor chimeras are used, wherein the signal-producing receptor chimera only comprises the extracellular region of the TSH receptor and the so-called anchor receptor chimera is a holoenzyme. From spring 2014, this method will be offered worldwide for automatic diagnosis of autoantibodies directed against the thyroid hormone receptor and is performed on the so-called Immulite® analyzer. The anchor receptor is bound onto plastic particles for example about 6 mm in diameter as the solid phase.

SUMMARY OF THE INVENTION

Also desirable is the application of the method of WO 2007/036511 A1 to fully automatic analytical devices which work with paramagnetic particles as the solid phase. Neither a test with the TSH receptor chimeras of WO 2007/036511 A1 nor a test with two TSH receptors which only comprise the extracellular domain of the TSH receptor enables the detection method to be performed on a fully automatic device which works with paramagnetic particles such as the ADVIA Centaur analyzer or the ARCHITECT analyzer.

The use of two extracellular TSH receptor chimeras (truncated TSH receptor chimeras) as anchor and as signal receptor, for performing the bridge assay described in WO 2007/036511 A1, showed too low a sensitivity and specificity for detecting autoantibodies against the TSH receptor. A measurement performed with this TSH receptor chimeras constellation was found to be non-reproducible, as is shown in Example 3 (Comparative example).

It is however extremely desirable to provide a method for detecting autoantibodies against the thyroid hormone receptor which has exactly the same accuracy and validity as the method described in WO 2007/036511 A1 and furthermore is possible on a fully automatic analyzer using paramagnetic particles as the solid phase.

This problem is solved by a method for detecting stimulating autoantibodies against the TSH receptor performable on a diagnostic analyzer, in which a patient sample is contacted with a first TSH receptor chimera bound to a solid phase, in order to bind stimulating autoantibodies against the TSH receptor possibly present in the patient sample onto the first TSH receptor chimera, an immune complex obtained is allowed to react with a second TSH receptor chimera, in order additionally to bind autoantibodies against the TSH receptor possibly present in the patient sample onto the second TSH receptor chimera and a reaction is performed to detect the immune complex containing the autoantibody, in which paramagnetic particles are used as the solid phase, the first and the second TSH receptor chimeras include the binding epitope for stimulating, but not for blocking or neutral autoantibodies against the TSH receptor, are N-terminally fused with a protein suitable for secretion of the TSH receptor into the extracellular space and the second TSH receptor chimera comprises a signaling amino acid sequence or another signaling marker for detecting the immune complex formed.

A further subject of the invention is a TSH receptor chimera which is N-terminally fused with a protein suitable for secretion of the TSH receptor into the extracellular space, and contains the binding epitope for stimulating autoantibodies against the TSH receptor but does not have the binding epitopes for blocking and neutral autoantibodies. An example of such an amino acid sequence is one which is at least 85%, preferably at least 90% and particularly preferably at least 95% identical with SEQ ID NO: 2, SEQ ID NO: 3, SEQ ID NO: 4 or SEQ ID NO: 6.

Also a subject of the invention is the use of a TSH receptor chimera which is N-terminally fused with a protein suitable for secretion of the TSH receptor into the extracellular space, and contains the binding epitope for stimulating autoantibody but not that for blocking or neutral autoantibodies against the TSH receptor. An example of such an amino acid sequence is one which is at least 85%, preferably at least 90% and particularly preferably at least 95% identical with SEQ ID NO: 2, SEQ ID NO: 3, SEQ ID NO: 4, or SEQ ID NO: 6, immobilized on paramagnetic particles, in a bridge assay on a diagnostic analyzer together with a further TSH receptor chimera for detecting autoantibodies against the thyroid hormone receptor (TSH receptor).

A further subject of the invention is the use of an extracellular domain of the wild type of the TSH receptor, which is N-terminally fused with a protein suitable for secretion the TSH receptor into the extracellular space, for example a serum protein, in a method for quantitative determination of autoantibodies against the TSH receptor.

Finally, a subject of the invention is the use of a fusion protein comprising the extracellular part of the wild type TSH receptor, which is N- or C-terminally fused with secretory alkaline phosphatase (SEAP) or another secretory protein, for example serum albumin, immobilized on paramagnetic particles, in a bridge assay for determining autoantibodies against the thyroid hormone receptor (TSH receptor).

Surprisingly, for the first time it was now possible to use two truncated TSH receptor chimeras in a bridge assay for detecting autoantibodies against the TSH receptor. Thus for the first time, from the complete TSH receptor or the complete TSH receptor chimera, essentially only the extracellular domain of the wild type receptor or the receptor chimera is used in a bridge assay. Surprisingly, it was further established that, as anchor receptor for an autoantibody a bound first TSH receptor chimera of a protein comprising the extracellular part of the TSH receptor immobilized on paramagnetic particles and as signal receptor a second TSH receptor chimera of a protein comprising the extracellular part of the TSH receptor, is suitable for detecting autoantibodies against the TSH receptor, if the extracellular part of the receptor is fused with a protein suitable for secretion of the TSH receptor into the extracellular space. The TSH receptor chimeras used according to the invention have high storage stability, transport stability, reservoir stability and also high assay stability. These statements also apply for the fusion protein from the extracellular domain of the wild type TSH receptor, which is N-terminally fused with a protein suitable for secretion of the TSH receptor into the extracellular space.

DESCRIPTION OF THE PREFERRED EMBODIMENTS

The TSH receptor extends from the cytosol through the cell membrane into the extracellular space. The extracellular portion of the receptor protein has the binding sites for TSH and the autoantibodies.

The receptor chimera according to the invention from the TSH receptor protein essentially comprises only the extracellular part of the TSH receptor. Essentially means that less than 40, preferably less than 30 or 20, particularly preferably less than 10 and down to 0 amino acids of the membrane part of the TSH receptor are present. This applies for the so-called first TSH receptor chimera used in the method according to the invention and also for the so-called second TSH receptor chimera additionally used. This applies also for the case in which the protein with the wild type of the TSH receptor is used. The TSH receptor chimera can for example comprise the amino acids 21 to 418 stating from the N-terminal part of the TSH receptor, preferably 21 to 380, particularly preferably 21 to 350 or 330 of the extracellular domain of the TSH receptor chimera. However, an extracellular domain of the TSH receptor which contains only the amino acids 21 to 260 is also usable according to the invention. If still fewer amino acids of the extracellular domain are used, the binding behavior of the epitope and the stability of the TSH receptor chimera changes. The same in turn also applies for the protein with the extracellular domain of the wild type of the TSH receptor. In this case, we understand wild type to mean an extracellular domain of the TSH receptor in which none of the amino acid sequences for binding stimulating, blocking or neutral autoantibodies have been replaced.

If the number of the amino acids of the TSH receptor chimera used according to the invention is too high, the secretion of the TSH receptor chimera from the recombinant cells used for its creation into the extracellular space during its production becomes worse.

The first and optionally the second TSH receptor chimera can additionally contain an amino acid sequence of the cytosolic part of the receptor. A preferable option for this are the amino acids 698-725 of the cytosolic part of the TSH receptor or part sequences thereof. Also, this is a highly immunogenic amino acid sequence which has proved advantageous for immobilizing the first TSH receptor chimera on the paramagnetic particles.

It has been found essential for performing the method according to the invention that the extracellular part of the receptor chimeras or the extracellular domain of the wild type of the TSH receptor is fused with a protein causing the secretion of the receptor chimera. Such a protein is for example a serum protein of a mammal. Albumin is preferably used. The fusion is preferably effected N-terminally. The first TSH receptor chimera used according to the invention particularly preferably contains a serum protein. Preferably albumin is used, which after fusion with the extracellular domain of the TSH receptor stabilizes the TSH receptor chimera and results in the secretion of the TSH receptor chimera used according to the invention from the cell in which the receptor chimera is generated. The same applies for a fusion protein of the extracellular domain of the wild type TSH receptor and a serum protein. The first TSH receptor chimera used according to the invention can also comprise only part sequences of a serum protein, in particular albumin protein, insofar as these ensure the stabilization of the TSH receptor chimera and the secretion from the cell. Through this measure, stability is imparted to the TSH receptor.

The second TSH receptor chimera used according to the invention has essentially the same structure as the first TSH receptor chimera used according to the invention. Since the second TSH receptor chimera in the method according to the invention has the function of a signal emitter, it must in that respect differ from the first TSH receptor chimera (anchor receptor). For this purpose, it has a marker. The marker can be N-terminally or C-terminally fused onto the second TSH receptor chimera. The marker is preferably C-terminally fused onto the second TSH receptor chimera. According to a preferred embodiment of the invention, the signal TSH receptor chimera has an N-terminal secretory alkaline phosphatase. The secretory alkaline phosphatase can also be used for a detection reaction. A further modification on the C-terminal part of the second TSH receptor chimera for the detection can then be omitted. Unless the detection is to be effected through another reaction.

Preferably therefore, the TSH receptor chimeras according to the invention are those wherein the cytosolic portion is completely or partly absent and the membrane part of the TSH wild type receptor preferably completely absent. The extracellular portion of the TSH receptor chimera according to the invention can further preferably be modified as explained below.

If stimulating autoantibodies are to be detected, a receptor chimera will preferably be used in which the sequence which binds blocking or neutral autoantibodies against the TSH receptor is replaced.

For the replacement, comparable sequences of another receptor which essentially display no binding for the particular two other types of autoantibodies are preferably used. Such comparable sequences can for example be sequences of a rat LG-CG receptor. Consequently in the TSH receptor chimeras used according to the invention the epitopes to which stimulating, neutral and/or blocking autoantibodies bind can be replaced. These receptor chimeras can be constructed according to Biochem. Biophys. Res. Comun. (1991), 179:70-77 or WO 01/27634 A2. Reference is made to both documents with regard to the creation of TSH receptor chimeras.

In the case of the detection of stimulating autoantibodies, the binding sequences for blocking and neutral antibodies in the TSH receptor protein are replaced by sequences of another receptor which cause no binding of the respective other type of autoantibodies. In the chimeras used for detecting stimulating autoantibodies, the TSH receptor amino acids 261 to 370 can preferably be replaced by the corresponding amino acids 261 to 329 of a rat LH-CGR.

Particularly advantageous on the TSH receptor chimeras according to the invention and the corresponding fusion protein with the extracellular domain of the wild type of the TSH receptor protein is that they are fused with an amino acid sequence for secretion of the TSH receptor chimera from the cell and thus during their production in recombinant cells, they are secreted into the extracellular space. Disintegration of cells to obtain the TSH receptor chimeras is then no longer necessary. Thus the TSH receptor chimera to be used according to the invention can be obtained with a high degree of purity and essentially without contamination with cell components which arise in the case of cell disintegration for obtention of the protein.

The second TSH receptor chimera used according to the invention or the corresponding fusion protein with the extracellular domain of the wild type TSH receptor (signal receptor) can be modified for detection, for example depending on the desired assay design, it can be fused with a marker. The labeling can be of such a nature that it provides a detectable signal directly or indirectly. Direct labeling in the sense of the invention is labeling of the TSH receptor chimera with a marker directly providing a detectable signal for detecting the immune complex. Indirect labeling in the sense of the invention can for example be the fusion of the TSH receptor chimera with an immunogenic peptide sequence which is recognized by a secondary labeled antibody suitable for detection.

Markers can be bound by fusion or chemical bonding with the TSH receptor chimera or the corresponding fusion protein with the extracellular domain of the wild type TSH receptor or the secondary antibodies. Suitable labeling is for example effected via enzymes such as alkaline phosphatase (AP), secretory alkaline phosphatase (SEAP), firefly or *Gaussia luciferase* and peroxidase or a dye such as an acridine dye, a fluorescent or bio/chemiluminescent material. In the case of the aforesaid enzymes, the nucleotide sequence coding for them is preferably fused with the nucleotide sequence of the second TSH receptor chimera (signal receptor). Suitable labeling is for example further effected with fluorescein isothiocyanate (FITC), biotinylation and streptavidin. In a preferred embodiment, the second TSH receptor chimera can be N-terminally fused with secretory alkaline phosphatase for detection.

In a further preferred embodiment, the second TSH receptor chimera is directly C-terminally labeled with an acridine dye.

In the method according to the invention, the so-called first TSH receptor chimera or the corresponding fusion protein with the extracellular domain of the wild type TSH receptor is bound to a paramagnetic solid phase during immune complex formation. The binding of the TSH receptor chimera to this solid phase can be effected via an immobilizing antibody, which is example directed against a C-terminal epitope of the TSH receptor chimera. Such an antibody can be a polyclonal antibody or a monoclonal antibody. For example, the immobilizing antibody can be directed against the amino acids 698-725 of the cytosolic part of the first TSH receptor chimera.

A secondary antibody can also be used for detecting the binding of an autoantibody to the TSH receptor chimera. The secondary antibody can be present in addition to the immobilizing antibody. It can be a monoclonal or a polyclonal antibody.

Suitable solid phases comprise paramagnetic particles, such as paramagnetic tubes, paramagnetic platelets and paramagnetic particles, but also other morphologies of paramagnetic particles. Such paramagnetic particles are known to those skilled in the art and are commercially available for example under the brand name Dynabeads® from Invitrogen Dynal AS. The paramagnetic particles used according to the invention as the solid phase can have a diameter of for example 0.5 μm to 5 μm. The particles can be paramagnetic or superparamagnetic.

The TSH receptor chimeras according to the invention can be stored lyophilized. They can be stored in lyophilized form bound to a solid phase via a monoclonal or polyclonal antibody. For the detection reaction, reconstitution of the lyophilized components is effected by dissolving in an assay buffer.

The TSH receptor chimeras according to the invention or the corresponding fusion protein with the extracellular domain of the wild type TSH receptor (referred to below as wild type variant) are of high stability in dissolved form (assay and reservoir stability). At 4° C. they remain stable for six to seven days and can be used for a further two to three weeks after renewed calibration of the diagnostic analyzer. At a temperature of 37° C., the dissolved TSH receptor chimeras according to the invention remain stable for six hours. These conditions are suitable for performing the detection method according to the invention on diagnostic analyzers, on which the components are stored at 4° C., while the test reaction can proceed without problems at 37° C. and thus in particular also on the Advia Centaur analyzer. In contrast to this, the holo-TSH receptor chimera remains stable for up to six days at 4° C., up to 48 hours at 24° C. and only three hours at 37° C.

To perform the method according to the invention, in each case a patient sample is treated with a first immobilized TSH receptor chimera (anchor receptor) and a second TSH receptor chimera (signal receptor) or the wild type variant thereof and tested for the relevant autoantibody.

Examples of embodiments of the method according to the invention are described below with reference to the figures.

FIGS. 1 and 2 diagrammatically show immune complexes immobilized on paramagnetic particles as a product of the method according to the invention.

FIG. 3, in particular 3.1 and 3.2, diagrammatically shows a first TSH receptor chimera (anchor receptor) usable in the method according to the invention. This is a construct of part sequences hTSHR with partial sequence replacement by rat LH/CG receptor fused with sequences of human albumin and an hTSHR anchor epitope. The cleavage sites are stated. The numberings of the amino acids relate to the respective amino acid or base of the holoreceptor.

Figure 6:
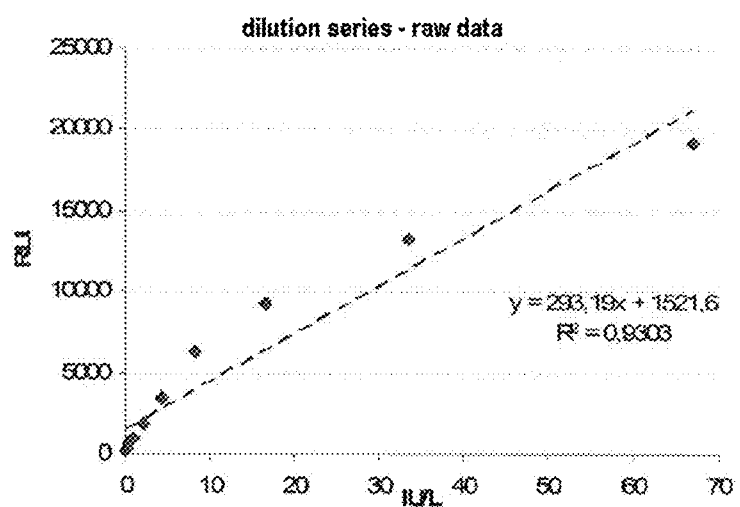

FIG. 6 shows the linearity of a dilution series of a patient serum with 66.5 IU/L. The measurements were made by the method according to the invention. The relative light unit RLU is given on the y axis, and the concentration of autoantibodies measured as international units per liter on the x axis.

Figure 7:
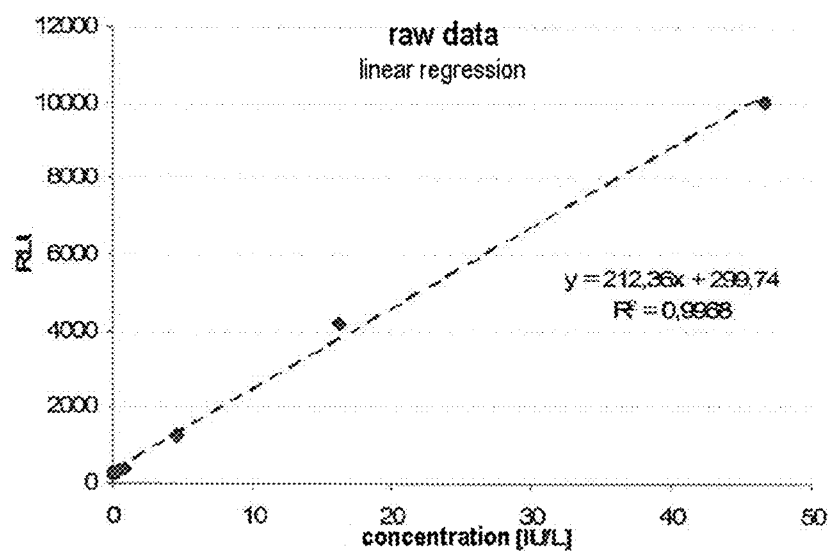

FIG. 7 shows measurements on a standard series which was calibrated with the sTRAB-DERA bridge assay of EP 1 929 311 B1. The calibration was performed with values in the microtiter plate test. The result shows that with the bridge assay according to the invention high linearity is also achieved.

Figure 8:
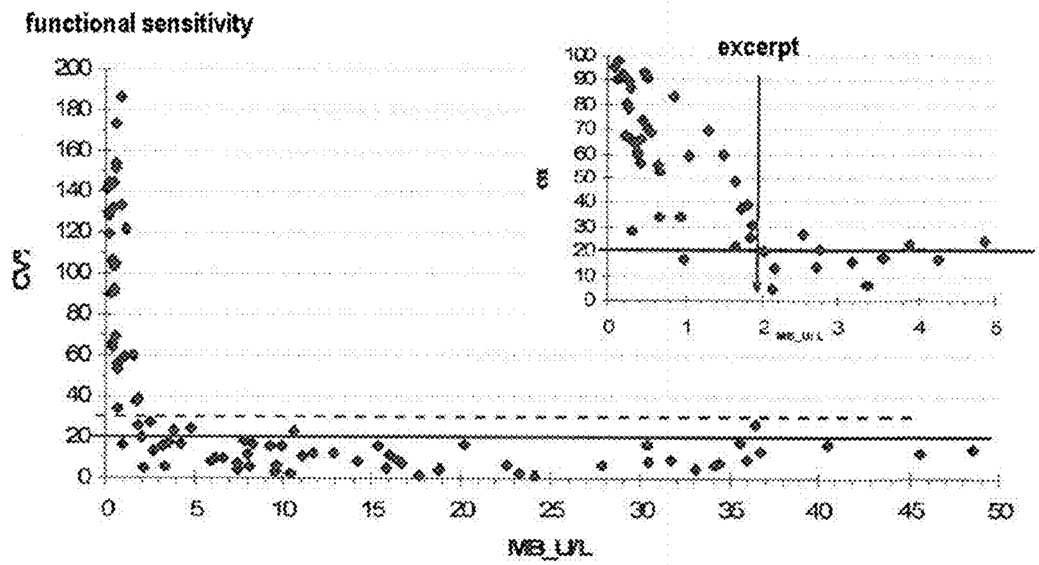

FIG. 8 serves to establish the functional sensitivity of the method according to the invention. The functional sensitivity here corresponds to the 20% limit in the interassay variance. Based on the determination of 114 sera and 17 sera pools (multiple determinations, n=3-7), the provisional functional sensitivity is at about 1.9 MB (Magnet Beads)_U/L. Taking account of increased fluctuation due to the manual performance of the assay, the functional sensitivity can alternatively be assessed with a limit of interassay variance of 30%; in this case, the value is at about 1.7 MB_U/L. The method according to the invention thus has very good sensitivity.

Figure 9:
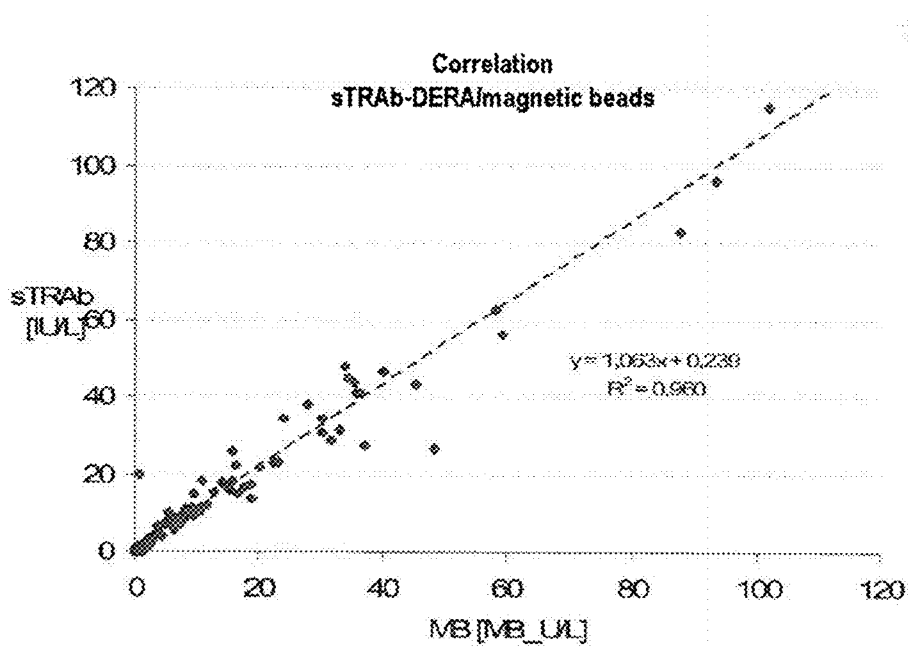

FIG. 9 shows a good correlation between results with magnetic beads assay (MB values) and sTRAb values (463 individual results from 114 sera and 17 sera pools).

SEQ ID NO: 1 shows the nucleotide sequence of an anchor receptor with the extracellular part of a TSH receptor chimera and a cytosolic amino acid sequence of a TSH receptor chimera N-terminally fused with human serum albumin including non-translated sequences.

SEQ ID NO: 2 shows the amino acid sequence to SEQ ID NO: 1. In SEQ ID NOs: 1 and 2 (first TSH receptor chimera or anchor receptor) the nucleotides 1 to 618 (amino acids 1-206) stand for the HSA peptide sequence, nucleotides 619 to 1553 (amino acids 207-516) for the TSHR sequence of the amino acids 21 to 330 of the chimera, nucleotides 1345 to 1553 (amino acids 446-516) for the LHR sequence of the amino acids 261 to 330 of the chimera, and nucleotides 1554 to 1637 (amino acids 516-543) for a highly immunogenic epitope from the cytosolic part of the TSH receptor (encoded by the nucleotides 743-763 of the TSH receptor).

SEQ ID NO: 3 shows a part sequence of the extracellular part of the TSH receptor. In SEQ ID NO: 5, the amino acids 1 to 240 stand for the amino acids 21 to 260 of the extracellular part of the TSH receptor (ECD260).

SEQ ID NO: 4 shows a further part sequence of the extracellular part of the TSH receptor chimera. In SEQ ID NO: 4, the amino acids 1 to 310 stand for the amino acids 21 to 330 of the extracellular part of the TSH receptor wherein the amino acids 241 to 310 are replaced by the corresponding amino acids 261 to 330 of a rat LH-CGR (ECD330).

SEQ ID NO: 5 shows a nucleotide sequence of a fusion protein from the extracellular domain of a wild type of the TSH receptor and a cytosolic amino acid sequence N-terminally fused with human serum albumin including non-translated sequences.

SEQ ID NO: 6 shows the amino acid sequence of a fusion protein from the extracellular part of a wild type of the TSH receptor and a cytosolic amino acid sequence N-terminally fused with human serum albumin including non-translated sequences.

Below, the implementation of the in vitro assay according to the invention for direct determination of stimulating TSH-R autoantibodies on paramagnetic microbeads as matrix on a microtiter plate is described.

Figure 3:
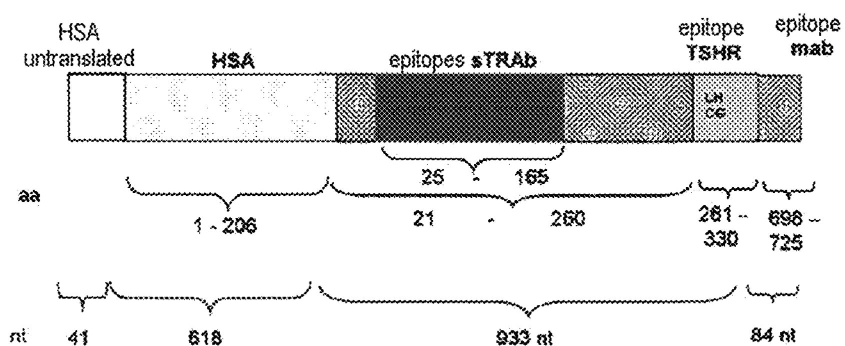
Figure 3:
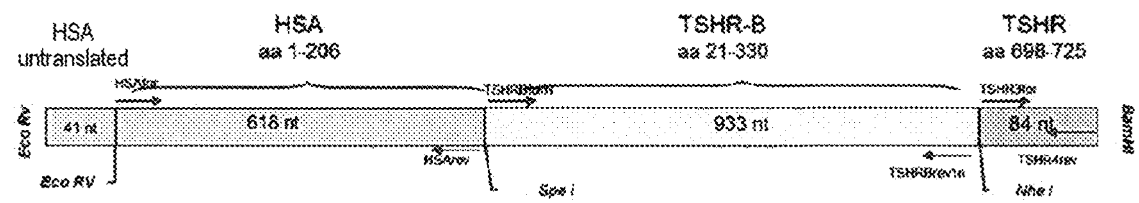

As anchor receptor on the paramagnetic microbeads as solid phase, a construct is produced by genetic engineering for the production of a fusion protein as shown in FIG. 3, which centrally contains a TSHR ECD (extracellular domain) with the amino acids (AA) 21-330. This is present as a chimera in which the AA 261-330 is replaced by a corresponding LH/CG-R sequence, so that no blocking antibody is also measured. At the C terminus, the cytosolic TSHR sequence of AA 698-725 is fused, to which a monoclonal antibody binds for the anchoring on the paramagnetic microbeads. At the N terminus, the part sequence of human serum albumin (AA 1-206) is fused. This HSA-ECD330-Chim serves as the secretory protein for the release of the whole fusion protein from the cultured cells in the medium. As a result, simpler production of the anchor receptor for binding autoantibodies is possible. This secreted receptor chimera differs by its high degree of purity from the complete wild type chimera, which after extraction from the cells is rendered impure by contamination with cell components. As well as the advantage of the secretion, it could for the first time be shown that this fusion protein, when it is coupled onto paramagnetic microbeads, has markedly higher stability in buffer and also in the mixture of buffer and patient serum.

Astonishingly, the human serum albumin (HSA) is of particular significance, since the coupling product consisting of paramagnetic microbeads and TSHR construct bound thereto via antibody remains stable (functional) on the analyzers for several days in dissolved form at 4° C. These are the necessary preconditions for an assay which uses paramagnetic microbeads as the solid phase. Under these dissolved conditions, the complete chimeric wild type receptor, which is present as an extract, very rapidly loses its functionality and therefore is not suitable for analyzers coupled on paramagnetic microbeads in solution. Astonishingly, the HSA is responsible for the stability of the fusion construct HSA-ECD330-Chim.

In a second assay step, patient serum is incubated in buffer solution with the coupling product HSA-ECD330-Chim described. Then the paramagnetic microbeads are bound onto a magnet, so that the factors influencing the sensitivity of the measurement are then eliminated by washing.

Figure 1:
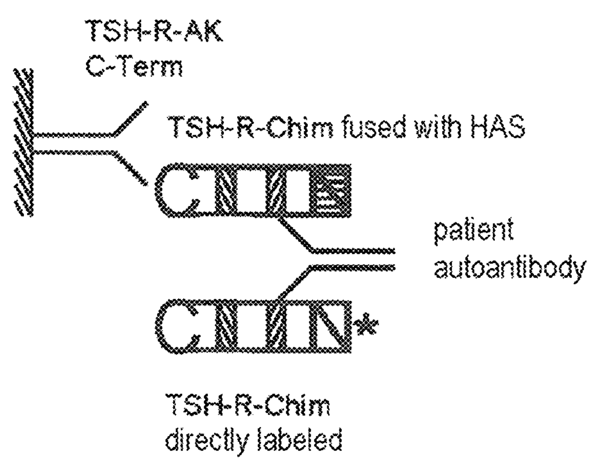
Figure 2:
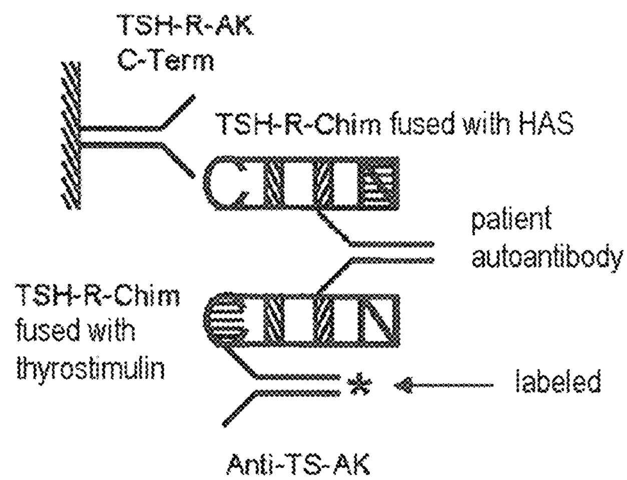

In the third assay step, the detection receptor which is also present recombinantly as a fusion protein is added to the reaction vessel. It contains the ECD centrally as a chimera in which the amino acids 261-266 are also replaced by corresponding LH/CG sequences. The detection receptor is N-terminally fused with SEAP (AA 1-520). The immune complex formed can then appear as shown diagrammatically in FIGS. 1 and 2. A magnet is always activated when liquids (sample, reagents, washing buffer) are to be removed from the reaction vessel. The quantification can be effected by chemiluminescence via SEAP activation; alternatively, the detection receptor can be labeled with acridinium esters.

According to one embodiment of the invention, the determination of stimulating autoantibodies can also be performed such that a measurement is performed in which a TSH receptor protein with the extracellular domain of the wild type receptor is used as a TSH receptor for binding the stimulating autoantibody instead of the TSH receptor chimeras. The value which was determined in the measurement with the TSH receptor chimeras for stimulating autoantibodies can be subtracted from the measured value thereby determined. In this way, non-stimulating autoantibodies, for example blocking and neutral autoantibodies, are also captured. This can be important for the clinical diagnosis of thyroid autoimmune diseases.

If the method according to the invention is used for the analysis of sera with blocking autoantibodies from patients who demonstrably have severe hypothyroidism requiring treatment, these are not detectable with the method according to the invention. This also points to the specificity of the method according to the invention.

The invention is further illustrated by the following examples.

Example 1 (Obtention of the TSH Receptor Chimeras)

Materials

For cloning the TSH receptor chimeras, the plasmid pcDNA3-rLHR (B9) from Dr. D. L. Segaloff (The University of Iowa, USA) was used.

The TSH receptor chimera in which a part sequence is replaced by a corresponding sequence of a rat LH-CGR was constructed according to the description in Biochem Biophys Res Commun. (1991), 179: 70-77. In this, the TSHR amino acids 261 to 370 were replaced by the comparable amino acids 261 to 329 of a rat LH-CGR.

The TSH receptor chimeras according to the invention and their wild type variant was produced by normal cloning methods with normal reagents.

Expression and Obtention of Fusion Proteins HSA2-TSHR ECD-B-330-mAb1 or TSHR/LH-CGR-SEAP as Cell Extract Confluent stable CHO-K1 and HEK293 cells respectively are grown in plates. The supernatant (about 8 mg/ml total protein) was collected and kept at −70° C. The supernatant thus obtained can be used in determination methods as HSA2-TSHR ECD-B-330-mAb1, TSHR-SEAP or TSHR/LH-CGR-SEAP respectively.

Obtention of the Secreted Extracellular Fusion TSHR Chimeras

The truncated, extracellular domains of the fusion TSH-R chimeras are secreted from the cells expressing them into the culture supernatant. The secreted receptor proteins are used directly in the experiment in the form of defined dilutions in the assay buffer. For example, 10 μl of extracellular SEAP-TSH-R chimera B from 5 ml of culture supernatant are used in a final dilution of 1:10 per determination.

Coupling of the Anchor Antibody onto Paramagnetic Particles 10 mg (330 μL) of tosylated Dynabeads® M-280 (Invitrogen Dynal AS) are withdrawn, washed twice with 1 ml of 0.1 M borate buffer pH 9.5 each time and then resuspended in 30 μl of borate buffer. For this, the following procedure is used in each washing step: the magnet is activated and the solution removed from the paramagnetic particles. Then the magnet is deactivated and 1 ml of 0.1 M borate buffer pH 9.5 is added to the paramagnetic particles and well shaken for a few seconds. This is followed by activation of the magnet and removal of the washing solution from the paramagnetic particles. The addition of 4.3 μg antibody (0.43 μg antibody/mg Dynabeads®) is effected. For this, anti-TSHR clone 3D7 is withdrawn and diluted to 30 μl with borate buffer. Furthermore, 30 μl per 100 μl Dynabeads® of a 3 M ammonium sulfate solution, treated with 0.1 M borate buffer pH 9.5 are added and thoroughly mixed. This is followed by an incubation for more than 20 hrs (overnight) at room temperature and with shaking in the overhead shaker. Next, they are washed twice with 1 ml of borate buffer each time as described above and 0.5 ml of freshly prepared blocking buffer (borate buffer, 0.5% BSA, 0.05% Tween 20) added. The dispersion is incubated for 2 hrs at 37° C. with shaking.

Next, the Dynabeads® are washed twice as described above with 1 ml of freshly prepared washing buffer (PBS pH 7.4, 0.1% BSA, 0.1% Tween 20). Then the supernatant is removed and the Dynabeads® coupled with anchor antibody are resuspended in 500 μl of washing buffer at a concentration of 20 mg/ml.

Coupling of the First TSH Receptor Chimera (Anchor Receptor) on Paramagnetic Particles 30 μl of a solution containing 20 mg/ml of Dynabeads® coupled with anchor antibody in buffer (PBS pH 7.4, 0.1% BSA, 0.1% Tween 20) are washed four times with 1 ml washing buffer (PBS pH 7.4, 0.1% BSA) and then 100 μl of the culture supernatant of an anchor receptor according to the invention (extracellular TSH receptor chimera N-terminally fused with HSA and C-terminally fused with a monoclonal antibody) were added. The resulting solution is incubated for 1 hr at room temperature with shaking. Next the supernatant is removed, the Dynabeads® washed twice with 1 ml washing buffer, resuspended in 30 μl washing buffer and stored at 4° C.

Example 2 (Performance of the Test According to the Invention)

Serum or plasma samples are produced from venous blood within 3 hours. Storage at 4° C. for a period of 7 days or at −20° C. for 1 to 2 years possible. Secondary antibodies (see above) are kept at −20° C. and thawed at room temperature before use in the test. TSH receptor chimeras are stored lyophilized on microtiter plates and reconstituted in buffer with protein stabilizers before use.

Per 2 ml reaction vessel, 30 μl of a solution containing 20 mg/ml Dynabeads® coupled with anchor receptor in washing buffer (PBS pH 7.4, 0.1% BSA) are diluted with 50 μL. After addition of 50 μl serum or plasma from the patient sample, the reaction vessel is incubated for 10 minutes at 37° C. with vigorous shaking. Next several washing steps are performed with activation/deactivation of the magnet as previously described, with 1 ml washing buffer each time. After addition of 100 μl of a solution of a signal receptor according to the invention (extracellular TSH receptor chimera N-terminally fused with secretory alkaline phosphatase (SEAP) diluted 1:5 in the washing buffer, the reaction vessel is incubated for 10 to at most 20 minutes at 37° C. with vigorous shaking. Next, several washing steps are performed with 1 ml washing buffer each time, as previously described. This is followed by the addition of 100 μl of undiluted 1,2-dioxetane-containing substrate solution (AP-x (AB) from p.j.k. GmbH, Kleinblittersdorf, Deutschland) and the reaction vessel is shaken for 30 minutes at room temperature with protection from light. The bio/chemiluminescence is measured with a tube luminometer. For this, the magnet is activated, and the solution removed from the paramagnetic particles and transferred to a measurement tube. The measurement tube is placed in the tube luminometer and the measurement of the bio/chemiluminescence performed according to the tube luminometer instructions.

Behavior of an sTRAb-DERA Calibrated Standard Series

To create the standard series, a standard solution WHO 90/672 with a standardized concentration of autoantibody was used. The starting solution of the standard contains 100 IU/1, which were diluted for the purposes of generating the standard curve. As the null value, the serum from a volunteer with no autoantibodies in TXBW buffer was used.

The TSH receptor chimeras used for binding stimulating autoantibodies are fixed onto Dynabeads® via antibody, stored lyophilized and are reconstituted in buffer containing protein stabilizers before use. The Triton X-100 washing buffer (TXWB) contains 0.1% TX-100, 50 mM Tris/HCl pH 8.0, 100 mM NaCl. The serum dilution buffer contains 5% glucose and 5% powdered milk in TXWB.

50 μl of sample solution (dilutions of the standard and null sample) per well are diluted 1:2 with dilution buffer and incubated on microtiter plates for 90 minutes at room temperature (about 22° C.). They are washed four times with 300 μl TXWB each time. This is followed by the addition of 10 μl of a 1:100 dilution of 5 ml culture supernatant from a culture dish of diameter 10 cm of extracellular TSH receptor chimera, fused with an enzyme SEAP, to 90 μl TXWB. This is then incubated with shaking (300-400 rpm) for 30 minutes at 37° C. This is then washed four times with 300 μl TXWB. The bio/chemiluminescence is measured with the Centrol® IA LB 296 microtiter plate measuring device from Berthold GmbH, Bad Wildbad, Schwarzwald, Germany using Tropix® (reagent for ECL (enhanced chemiluminescence) from Applied Biosystems, Foster City, Calif., USA).

The detection limit is about 0.2 IU/1. There exists a polynomial function between relative light units (RLU=Relative Light Unit) and the concentration of the standard for stimulating autoantibodies over range which extends up to at least 40 IU/1.

Example 3 (Comparative Example)

In this example, on the one hand two truncated TSH receptor chimeras and on the other a pure holoreceptor chimera were used as anchor receptor and a truncated receptor chimera (ECD) as signal receptor according to EP 1 929 311 B1. The anchor receptor chimera was immobilized on the plastic wall of the microtiter plate.

The anchor antibody (10.75 mM citric acid; 69 mM HEPES; 50% glycerol; pH 7.0) incubated overnight at 4° C. in carbonate buffer (100 mM NaCO3/NaHCO3 pH 9.6) as 10 μg/ml on the microtiter plate (MTP 96 wells). After washing four times (300 μl per well) with assay buffer (0.1% Triton X-100; 50 mM Tris-HCl pH 8.0; 100 mM NaCl) the blocking of the free MTP surface is effected for 1 hour at 37° C. with blocking solution (5% milk powder; 5% glucose in carbonate buffer). This is followed by coating of the solid phase with anchor receptors in assay buffer for 1 hour at 20-24° C. with shaking (300 rpm). Holoreceptor chimeras are used as cell extract (in 1% Triton X-100; 150 mM NaCl; 50 mM Tris-HCl pH 8.0; Complete® protease inhibitors) used with a concentration of total protein of 500 μg/ml (up to 2000 μg/ml depending on receptor chimera). Secreted ECD receptor chimeras are used as cell culture supernatant (in RPMI 1640; 10% FCS; 1% penicillin/streptomycin [10, 000 U, 10,000 μg/ml]) at a concentration of 10-100% in assay buffer after clone-dependently defined production of the supernatants. This is followed by fourfold washing (300 μl per well) with assay buffer. Optionally, lyophilization drying of the MTPs is possible. For this, the washing after the anchor receptor incubation is effected only twice with assay buffer followed by twofold washing with lyophilization buffer (50 mM HEPES-NaOH pH 6.5; 0.1% Triton X-100; 5% milk powder; 3% Karion). The last washing step takes place with an extended MTP incubation time (5-10 mins). The MTPs are immediately shock frozen in the nitrogen gas phase (−180° C. to −130° C.) (minimum incubation 30 mins) and then lyophilized (0.011 mbar/−60° C., 4-24 hours depending on number of MTPs).

The patient serum (optionally after reconstitution of dried MTPs for 5-10 mins in assay buffer) is incubated diluted 1:2 in assay buffer for 90 mins at 20-24° C. with shaking (300 rpm). To remove the unbound material, these are washed four times with assay buffer. The incubation of the detection receptor is effected in assay buffer for 30 mins with shaking (300 rpm), at 37° C. with secreted ECD receptor chimeras and at 20-24° C. with holoreceptor chimeras. The concentration used is 1000 μg/ml total protein (up to 3000 μg/ml depending on receptor chimera) with cell extracts of holoreceptor chimeras and with secreted ECD receptor chimeras 10-100% depending on the clone, after clone-dependently defined production of the supernatants. This is followed by fourfold washing with 300 μl assay buffer per well each time. The detection is effected by addition of substrate (135 μM CDP-Star or alternatively AP substrate 1:1.5 [to 3] in 1.0 M diethanolamine pH 9.8; 0.5 mM $MgCl_2$; 0.0001% xylene cyanol) with incubation for 30 mins at 20-24° C. with shaking (300 rpm) followed by quantification in the microtiter plate luminometer.

Stability measurements of the detection receptor chimeras are performed by preincubation for various periods of time followed by use in the bridge assay, wherein the anchor receptor chimera is treated as in the bridge assay on which the application is based, i.e. it is bound quasi affinity chromatographically on the solid phase.

Figure 5:
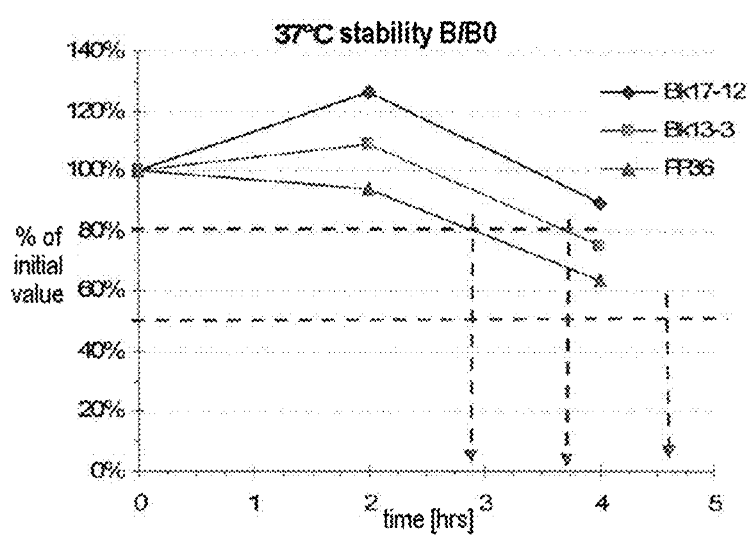
FIG. 5 shows the assay stability of the anchor receptor which is immobilized on paramagnetic particles with an anchor antibody on incubation at 37° C. and at 4° C. without shaking. After 3 hours and 3.75 hours respectively, about 80% or more of the anchor receptor is still intact.

The measurement results of the comparison are microtiter plate experiments. The results are shown in FIG. 5. The microtiter plates were coated at 4° C. with an antibody onto which the anchor receptor chimera (holoreceptor chimera or ECD receptor chimera (comparison)) had been bound. The incubation with patient serum took place at room temperature.

Figure 4:
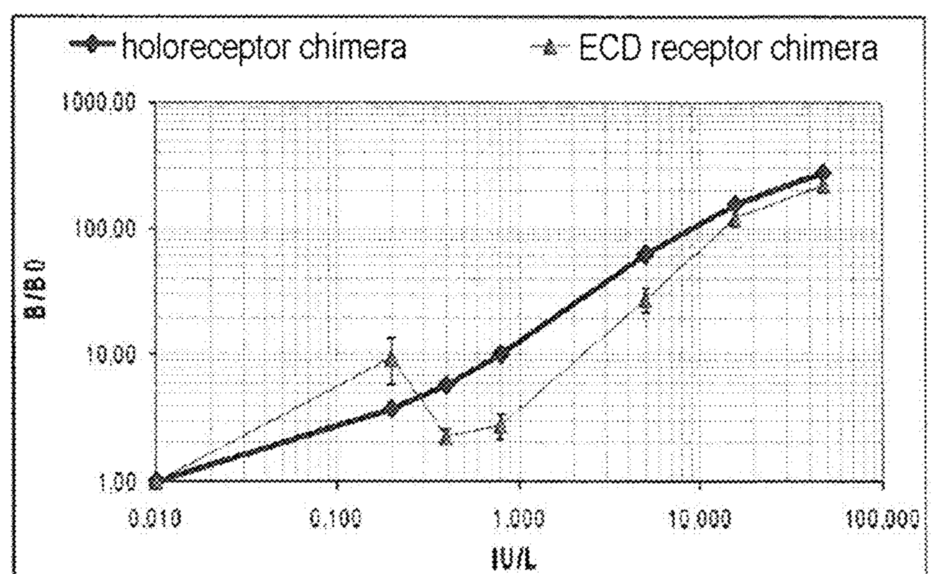
FIG. 4 shows the results of the comparative example. The results are explained in the comparative example.

Finally, the measurement values curves obtained in FIG. 4 are two calibration curves, wherein the quotient B/B0 (bound/unbound) plotted on the ordinates was used in order to exclude nonspecific binding in the result. The autoantibody units of a standardized sample are given on the abscissa.

The bold-printed curve shows the embodiment with a first TSH receptor chimera bound to a solid phase (holoreceptor chimera) and a second truncated TSH receptor chimera (ECD receptor chimera), which contains only the extracellular part of the holoreceptor as signal receptor. In the case of the normally printed curve, the truncated receptor chimera (ECD receptor chimera) is likewise used as the anchor receptor chimera instead of the first TSH receptor chimera (holoreceptor chimera) bound onto a solid phase.

Comparison of the course of the two curves shows marked differences in the binding behavior of the autoantibodies onto the holo- and truncated receptor chimeras. The curve for the measured values of the samples with two ECD receptor chimeras (anchor and signal receptor are ECD receptor chimeras) "is jagged", is not reproducible and does not yield the required sensitivity and specificity. In particular, it is unsuitable for a broad concentration range. The use of a holoreceptor chimera as anchor receptor and a further holoreceptor chimera is thus suitable neither for microtiter plate experiments nor for determination on an automatic device.

The invention claimed is:

1. A method for detecting stimulating autoantibodies against the thyroid stimulating hormone (TSH) receptor in a patient sample, said method comprising:

a) contacting a patient sample with a first TSH receptor chimera bound to a solid phase in order to bind stimulating autoantibody against the TSH receptor possibly present in the patient sample onto the first TSH receptor chimera, to obtain an immune complex comprising the stimulating autoantibody and first TSH receptor chimera, b) reacting the immune complex obtained in step a) with a second TSH receptor chimera, in order to obtain the stimulating autoantibody against the TSH receptor possibly present in the patient sample bound with an immune complex with the first and second TSH receptor chimeras, c) performing a reaction to detect the stimulating autoantibody bound in the immune complex obtained in step b), wherein the TSH receptor chimeras do not present binding epitopes for neutral and blocking autoantibodies against the TSH receptor, wherein the solid phase comprises paramagnetic particles, wherein the first TSH receptor chimera comprises:

i) an extracellular portion of the TSH receptor, wherein this extracellular portion consists of the full length amino acid sequence as set forth in SEQ ID NO: 3 or SEQ ID NO: 4, ii) said amino acid sequence in i) comprises the binding epitope for stimulating autoantibodies against the TSH receptor, iii) a protein suitable for the secretion of the TSH receptor chimera into the extracellular space, which is fused to said amino acid sequence in i), and iv) a human serum albumin peptide sequence fused to the N-terminus of the first TSH receptor chimera;

and is immobilized on the solid phase, wherein the second TSH receptor chimera comprises:

i) an extracellular portion of the TSH receptor, wherein this extracellular portion consists of the full length amino acid sequence as set forth in SEQ ID NO: 3 or SEQ ID NO: 4, ii) said amino acid sequence in i) comprises a binding epitope for stimulating autoantibodies against the TSH receptor, iii) a protein suitable for the secretion of the TSH receptor into the extracellular space, which is fused to said amino acid sequence in i), and iv) a signaling amino acid sequence or another signaling marker for detecting said immune complex formed, and d) determining that stimulating autoantibodies against the TSH receptor are present in the patient sample if the immune complex comprising the first and second TSH receptor chimeras is detected in step c).

2. The method according to claim 1, wherein the first and/or the second TSH receptor chimera is N-terminally fused with a human serum protein.

3. The method according to claim 1, wherein the second TSH receptor chimera is N-terminally or C-terminally fused with secretory alkaline phosphatase.

4. The method according to claim 1, wherein the signaling marker is secretory alkaline phosphatase, a firefly or *Gaussia luciferase* or a peroxidase.

5. The method according to claim 1, wherein the signaling marker is an acridine or ruthenium compound or fluorescein isothiocyanate compound.

6. The method according to claim 1, wherein the immune complex bound on the paramagnetic particles is detected using an immunoassay analyzer.

* * * * *